(12) United States Patent
Nielsen

(10) Patent No.: US 7,771,400 B2
(45) Date of Patent: Aug. 10, 2010

(54) INJECTION DEVICE

(75) Inventor: Lars Ulrik Nielsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/407,447

(22) Filed: Mar. 19, 2009

(65) Prior Publication Data

US 2009/0234299 A1     Sep. 17, 2009

Related U.S. Application Data

(63) Continuation of application No. 11/995,005, filed as application No. PCT/EP2006/063724 on Jun. 30, 2006, now abandoned.

(60) Provisional application No. 60/712,553, filed on Aug. 30, 2005.

(30) Foreign Application Priority Data

Jul. 8, 2005     (EP)     ................... 05106254

(51) Int. Cl.
*A61M 5/00*     (2006.01)

(52) U.S. Cl. .................. 604/211; 604/207; 604/208; 604/224; 604/228

(58) Field of Classification Search ................ 604/151, 604/207–211, 218, 224, 232, 228
See application file for complete search history.

(56) References Cited

U.S. PATENT DOCUMENTS

| | | | | |
|---|---|---|---|---|
| 5,545,147 | A | * | 8/1996 | Harris ..................... 604/209 |
| 5,626,566 | A | * | 5/1997 | Petersen et al. ............. 604/208 |
| 6,004,297 | A | | 12/1999 | Steenfeldt-Jensen et al. |
| 2005/0033244 | A1 | | 2/2005 | Veasey et al. |

FOREIGN PATENT DOCUMENTS

| | | |
|---|---|---|
| EP | 1541185 | 6/2005 |
| WO | WO 2004/078239 | 9/2004 |

* cited by examiner

*Primary Examiner*—Kevin C Sirmons
*Assistant Examiner*—Bhisma Mehta
(74) *Attorney, Agent, or Firm*—Marc A. Began

(57) ABSTRACT

An injection device with a travelling clutch which can be shifted between two different positions by the activation of an injection button. In the first position, the injection button and the drive sleeve is allowed to rotate relatively to the piston rod, which is blocked from rotation by the clicker element. In the second position, the drive sleeve and the injection button is axially movable while the piston rod is allowed to rotate.

7 Claims, 2 Drawing Sheets

INJECTION DEVICE

CROSS-REFERENCE TO RELATED APPLICATIONS

This application is a continuation of U.S. application Ser. No. 11/995,005, filed Jan. 28, 2008 (now abandoned), which is a 35 U.S.C. §371 national stage application of International Patent Application PCT/EP2006/063724 (published as WO 2007/006662), filed Jun. 30, 2006, which claimed priority of European Patent Application 05106254.5, filed Jul. 8, 2005; this application further claims priority under 35 U.S.C. §119 of U.S. Provisional Application 60/712,553, filed Aug. 30, 2005.

THE TECHNICAL FIELD OF THE INVENTION

The invention relates to an apparatus such as an injection pen for delivering a liquid drug to the human body preferably in a subcutaneous way and especially to an injection device with a piston rod having two threads.

DESCRIPTION OF RELATED ART

In the disclosure of the present invention reference is mainly made to the treatment of diabetes by injection of insulin; however this is only an exemplary use of the present invention.

Injection pens are mainly made for users who have to inject themselves frequently, e.g. people suffering from diabetes. A number of demands are set to such injection pens. The setting of a dose must be easy an unambiguous and it must be easy to read the set dose. It must be possible with a minimum of trouble to cancel or change a wrongly set dose and when the dose is injected the dose setting must return to zero. When a prefilled injection pen is in question, i.e. an injection pen which is disposed of when the reservoir is empty, the injection pen must further be cheap and made of materials suitable for recycling.

Most dose setting devices work with a threaded piston rod co-operating with a nut where the nut and the piston rod may be rotated relative to each other. The dose setting may be obtained by screwing the nut away from a stop to which it is return during injection by pressing the piston rod forward until the nut member abuts the stop. By other dose setting devices one of the elements, the nut or the piston rod, is kept inrotatable and the other is allowed to rotate a set angle depending on the set dose, whereby the piston rod is screwed forward a distance through the nut member.

A prior art delivery apparatus fulfilling the above is disclosed in U.S. Pat. No. 6,004,297. The apparatus disclosed in the embodiment depictured in FIG. 6 to 10 comprises a piston rod having a proximal thread and a distal thread. The proximal thread is engaged by a driver and the distal thread is engaged by a thread in the part of the housing bridging the dose setting and injection part with the cartridge holder part.

A dose is set by rotating the driver up the proximal thread of the piston rod and injected by returning the driver axially. In order to secure that the set number of doses are actually expelled it is important that the driver is only axially returned i.e. it is important to prevent the driver from rotating down the proximal thread during injection.

In order to secure the driver against rotation when injecting, a number of grooves are provided on the driver which grooves are engages by one or more protrusions on the inside surface of the housing.

A similar injection pen is disclosed in WO 04/078239. This injection pen also comprises a threaded piston rod having two different threads. Here the driver is axially locked during injection by use of a clicker element engaging the clutch.

DESCRIPTION OF THE INVENTION

Having regard to the above-identified prior art devices, it is an object of the present invention to provide a drug delivery device which eliminates disadvantages in the prior art drug delivery device and provides an improved locking of the driver during injection.

The coupling or travelling clutch located between the piston rod, the drive sleeve, and the injection button is designed such that the drive sleeve and the injection button is allowed to rotate relatively to the piston rod, which is blocked from rotation by the clicker element, when setting a dose.

During injection, the drive sleeve and the injection button is moved axially back while forcing the piston rod to rotate.

The coupling or clutch comprises a slider element which is secured in the housing such that the slider can only move axially relatively to the housing.

Further a clicker element is provided which is connected to the slider to follow the axial movement of the slider however the clicker element can rotate relatively to the slider. A movable element of the clicker element is engaged by the slider such the clicker element can be shifted between two different positions relatively to the slider; A first position where the clicker element is both axially and rotational locked to the slider and a second position where the clicker element is only axially locked to slider but free to rotate relatively to the slider.

To shift the engagement of the clicker element and the slider from the first position to the second position, the injection button is used, preferably, such that an axial movement of the injection button accomplish the shift.

DEFINITIONS

An "injection pen" is typically a mechanical i.e. user energized injection apparatus having an oblong or elongated shape somewhat like a pen for writing. Although such pens usually have a tubular cross-section, they could easily have a different cross-section such as triangular, rectangular or square.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

Further the term "injection needle" defines a piercing member adapted to penetrate the skin of a subject for the purpose of delivering or removing a liquid.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device carrying the injection needle whereas the term "proximal end" is meant to refer to the opposite end pointing away from the injection needle.

Figure 1:
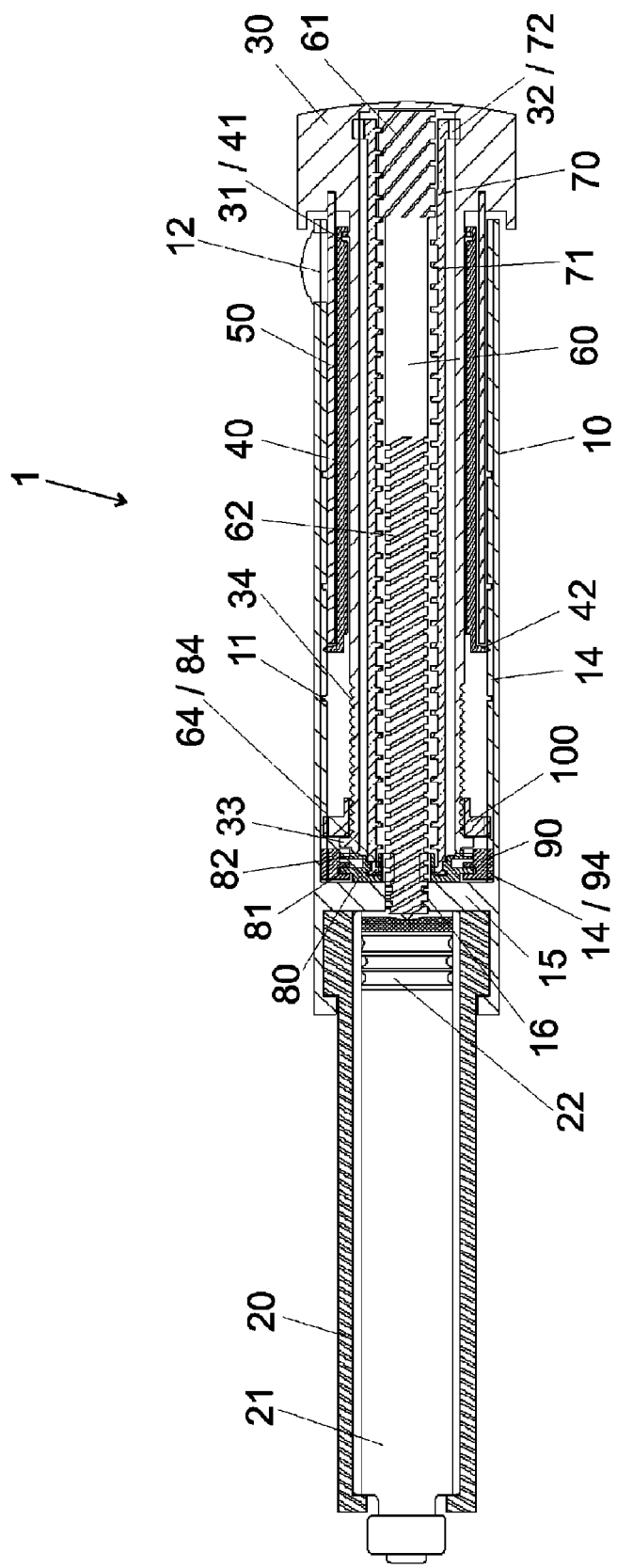
FIG. 1 Shows a cross section of an injection device according to the present invention.
Figure 2:
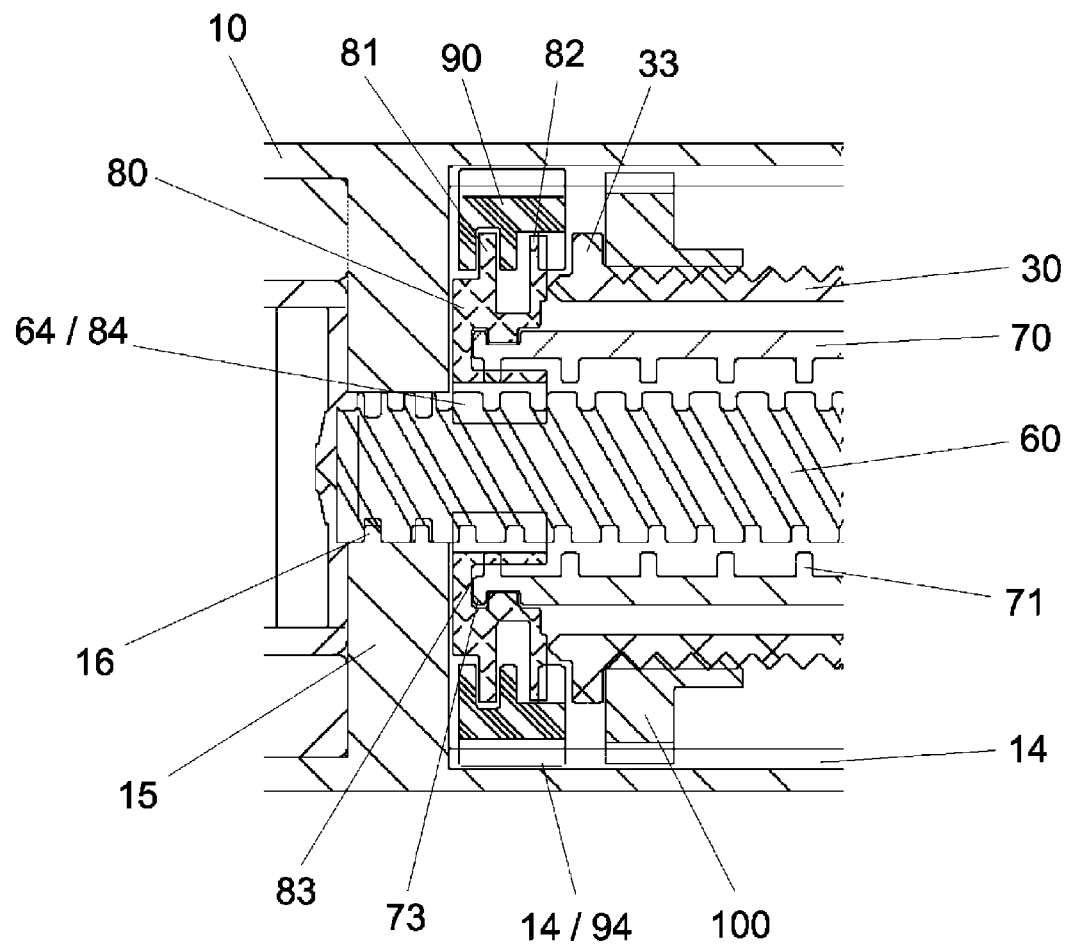
FIG. 2 Shows a cross section of a part of FIG. 1 in a first position.

FIG. 1 discloses a pen-shaped injection device 1 comprising a proximal housing 10 holding the dose setting and injection mechanics at its proximal end and a distal cartridge holder 20 holding a cartridge 21 containing the liquid drug at its distal end. The housing 10 is provided with an internal thread 11 and an opening 12 through which a user can view the dose setting preferably through a magnifier.

At the most proximal end of the housing 10, an injection button 30 is supported. This injection button 30 has a longitudinal shape and is interfaced with a dose dial sleeve 40 through a rotatable connection 31/41. The dose dial sleeve 40 is at its distal end 42 guided in the internal thread 11 of the housing 10. The dose dial sleeve 40 is covered by a transparent shield 50 which is inrotatable connected to the injection button 30 or alternatively moulded as a part of the injection button 30.

Centrally in the injection device 1 a piston rod 60 is provided. This piston rod 60, which preferably has a non-circular cross-section, has a proximal thread 61 and a distal thread 62, which preferably has a different pitch. The distal thread 62 is engaged by a thread 16 internally in the part 15, which may be a nut member, of the housing 10 bridging the housing 10 to the cartridge holder 20 such that the piston rod 60 can be screwed out of this thread 16 and into the cartridge holder 20 by rotation. The part 15 of the housing 10 bridging the housing 10 to the cartridge holder 20 could be provided as a separate part 15 connected either to the housing 10 or to the cartridge holder 20 in a way making it not axially displaceable. The proximal thread 61 is engaged by a driver 70, which may be a drive sleeve, having an internal thread 71 engaging the proximal thread 61. Further the driver 70 is connected to the injection button 30 through a connection 32/72 making the driver 70 rotatable with the injection button 30 but axially displaceable.

A releasable coupling is operational between a first position and a second position and is provided between the piston rod 60 and the drive sleeve 70. The coupling, in the first position, prevents rotation of the piston rod 60 while allowing rotation of the drive sleeve 70 and, in the second position, prevents rotation of the drive sleeve 70 whilst allowing rotation of the piston rod 60. The coupling may comprise a clicker element 80 and a slider 90. The clicker element 80 which is inrotatable secured to the piston rod 60 through a coupling 64/84 is located distally in the housing 10. The clicker element 80 comprises a distal ring element 81 and a proximal ring element 82. The distal ring element 81 is secured in the slider 90 in a way making the clicker element 80 rotatable relatively to the slider 90 but axially coupled to the slider 90.

The proximal ring element 82 engages the slider 90 such that the clicker element 80 is locked to the slider 90 which again is locked to the housing 10 through the axially displaceable connection 14/94, however since the proximal ring element 82 is flexible it can be pushed out of engagement with the slider 90 by providing an axially force on the proximal ring element 82.

The clicker element 80 is further provided with a circular track 83 which is engaged by a similar protrusion 73 on the driver 70 making the clicker element 80 and the driver 70 relatively rotatable but axially connected.

The injection button 30 is distally provided with an End-of-Content (EoC) thread 34 engaged by an EoC nut member 100 slidable in a longitudinal track 14 in the housing 10. A description of a similar EoC mechanism is provided in EP 1.250.167.

When a user wants to set a dose, the injection button 30 is rotated which due to the connection 32/72 forces the driver 70 to rotate up the proximal thread 61 on the piston rod 60. During dose setting, the piston rod 60 is secured against rotation by the connection 64/84 with the clicker element 80 which is locked to the housing 10 by the engagement between the proximal ring element 82 and the slider 90.

As the driver 70 rotates up the proximal thread 61, the dose dial sleeve 40 is pulled backwards out of the housing 10 by the engagement 31/41, however since the dose dial sleeve 40 is guided in the internal thread 11 in the housing 10 it rotates. The shield 50 surrounding the dose dial sleeve 40 is also rotated with the injection button 30.

The clicker element 80 which is rotatable mounted to the driver 70 is moved axially in the proximal direction without rotation due to the engagement with the slider 90 which slides in a track 14 on the inside surface of the housing 10.

In order to inject the set dose, the user places a finger on the injection button 30 and exerts an axial force. This will first move the injection button 30 a few millimetres relatively to the driver 70 and an axial force will be exerted on the proximal ring element 82 of the clicker element 80 which will release the clicker element 80 from the slider 90. At the same time the distal protrusion 33 on the injection button 30 will engage the slider 90 such that the injection button 30 is forced to move axially without rotating.

With the driver 70 rotational locked to the injection button 30 through the connection 32/72 and a continuous axial movement of the injection button 30, the piston rod 60 is forced to rotate. Since the coupling is rotational locked to the piston rod 60, the coupling will rotate as well. This rotation being allowed since the clicker element 80 is no longer locked to the slider 90.

The continuous axial forward movement of the injection button 30 and the driver 70 will force the piston rod 60 to rotate and be screwed forward in the thread 16. A forward movement of the piston rod 60 will force a rubber plunger 22 to move forward inside the cartridge 21 and expel a volume of the liquid drug inside in the cartridge 21 out through a not shown conduit such as an injection needle mounted to the distal end of the cartridge 21.

Some preferred embodiments have been shown in the foregoing, but it should be stressed that the invention is not limited to these, but may be embodied in other ways within the subject matter defined in the following claims.

The invention claimed is:

1. A drug delivery device comprising:
   a housing,
   a piston rod having a proximal thread and a distal thread,
   a nut member which is not axially displaceable in the housing and which has an inner thread mating the distal thread of the piston rod such that the piston rod is screwed in a distal direction when rotated relatively to the nut member,
   a drive sleeve which has an inner thread mating the proximal thread of the piston rod such that the piston rod is rotated when the drive sleeve is axially moved relatively to the piston rod
   wherein a releasable coupling operational between a first position and a second position is provided between the piston rod and the drive sleeve, wherein the coupling in the first position prevents rotation of the piston rod while allowing rotation of the drive sleeve and in the second position prevents rotation of the drive sleeve whilst allowing rotation of the piston rod.

2. A drug delivery device according to claim 1 wherein the coupling comprises a slider slidable connected to the housing.

3. A drug delivery device according to claim 2 wherein the coupling comprises a clicker element coupled to the slider.

4. A drug delivery device according to claim 3 wherein the clicker element is both axially and rotational locked to the slider in the first position.

5. A drug delivery device according to claim 3 wherein the clicker element is rotational released from the slider in the second position.

6. A drug delivery device according to claim 5 wherein the clicker element is shifted between its locked and its released position by axial movement of an injection button.

7. A drug delivery device according to claim 6 wherein the injection button is connected to the drive sleeve in a way making the injection button axially displaceable relatively to the drive sleeve.

* * * * *